US00PP26684P3

(12) United States Plant Patent
Case, Jr.

(10) Patent No.: US PP26,684 P3
(45) Date of Patent: May 3, 2016

(54) *THUJA* HYBRID PLANT NAMED 'BFC68'

(50) Latin Name: *Thuja plicata×standishii*
Varietal Denomination: BFC68

(71) Applicant: Benjamin Frank Case, Jr., Suffolk, VA (US)

(72) Inventor: Benjamin Frank Case, Jr., Suffolk, VA (US)

( * ) Notice: Subject to any disclaimer, the term of this patent is extended or adjusted under 35 U.S.C. 154(b) by 112 days.

(21) Appl. No.: 14/120,400

(22) Filed: May 16, 2014

(65) Prior Publication Data

US 2015/0334891 P1 Nov. 19, 2015

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

JC Raulston Arboretum at NC State University, retrieved on Oct. 27, 2015, retrieved from the Internet at <http://jcra.ncsu.edu/horticulture/our-plants/plant-mapping.php?serial=75857> 3 pp.).*

* cited by examiner

*Primary Examiner* — June Hwu
(74) *Attorney, Agent, or Firm* — Samuel R. McCoy, Jr.

(57) ABSTRACT

'BFC68' is a distinctive variety of *Thuja plicata×standishii* which is characterized by the combination of an overall smaller plant size, dense foliage at the plant's apex where normally there are few branches or branchlets, a higher degree of branching among first, secondary and tertiary branchlets, a pendulous attitude of the terminal portion of lateral branches and all branchlets which creates a soft, feathered foliage texture, and stability and uniformity of traits through successive cycles of asexual propagation.

6 Drawing Sheets

Latin name of the genus and species: The Latin name of the genus and species of the novel variety disclosed herein is *Thuja plicata×standishii*.

Variety denomination: The inventive variety of *Thuja plicata×standishii* disclosed herein has been given the variety denomination 'BFC68'.

BACKGROUND OF THE INVENTION

The present invention relates to a new and distinct perennial variety of *Thuja plicata×standishii*, which has been given the variety denomination of 'BFC68'. Both *Thuja plicata* and *Thuja standishii*, commonly known as arborvitae, are coniferous evergreens of the cypress family Cupressaceae. While members of the same family, their origins and morphological characteristics vary greatly. *Thuja plicata* is a large evergreen tree that is native to northwestern North America whereas *T. standishii* is a small to medium evergreen that is native to southern and central Japan. *T. plicata* can grow to a size of 70 ft tall by 25 ft wide whereas *T. standishii* is typically reported to grow to more than 30 ft tall and 15 ft wide, at maturity. Despite the difference in size, both species have similar pyramidal growth habits and foliage with sprays of scale-like foliage borne on horizontal to ascending branches and branchlets. Both are hardy in USDA Zones 5 through 7. The most prolific hybrid of the two species, and the parent plant of the candidate variety, *Thuja plicata×standishii* 'Green Giant' is favored by home gardeners and professionals alike for its vigorous growth habit, intermediate size, pyramidal to conical shape and rich green foliage color that persists outstanding throughout its hardiness range.

Parentage: The *Thuja plicata×standishii* variety 'BFC68' was first observed on Apr. 25, 2007 as a spontaneous mutation of *Thuja plicata×standishii* 'Green Giant' (unpatented) vegetative cuttings propagules. In January of 2002, vegetative cuttings were taken from stock plants of 'Green Giant' at Old Courthouse Nursery in Warsaw, N.C. On Mar. 16, 2004, the breeder took delivery of 220 3-gallon nursery stock plants of 'Green Giant' at Plantation Spring Nursery in Suffolk Va., said stock plants being progeny of the aforementioned vegetative cuttings of 2002. These plants were transplanted into the ground for field production in order to further grow them to a sellable size. On Apr. 25, 2007 as the breeder was harvesting some of the resulting sellable plants, one plant was discovered that exhibited growth characteristics which were distinctly different from either the parent plant or other progeny within the same crop. This plant, now called 'BFC68', was noted as having an overall smaller plant size, dense foliage from the plant's base to the apex where normally there are few branches, a higher degree of branching among branchlets, and also a slightly pendulous branchlet attitude which gave the plant a softer foliage texture. The plant was isolated for further evaluation and to confirm the characteristics initially noted in the field.

Asexual Reproduction: 'BFC68' was subsequently propagated by vegetative stem cuttings, at the inventor's nursery in Suffolk Va., through three successive generations, from 2007 to 2012, and the resulting progeny maintained the distinguishing characteristics of the original plant. In September of 2012, the breeder made the final determination that the characteristics of the original plant discovered in April of 2007 had remained true and stable through each successive generation; the plant was named 'BFC68'.

SUMMARY OF THE INVENTION

'BFC68' is a distinctive variety of *Thuja plicata×standishii* which is characterized by the combination an overall smaller plant size, dense foliage at the plant's apex where normally there are few branches or branchlets, a higher degree of branching among first, secondary and tertiary branchlets, and a pendulous attitude of the terminal portion of lateral branches and all branchlets which creates a soft, feathered foliage texture.

BOTANICAL DESCRIPTION OF THE PLANT

Figure 1:
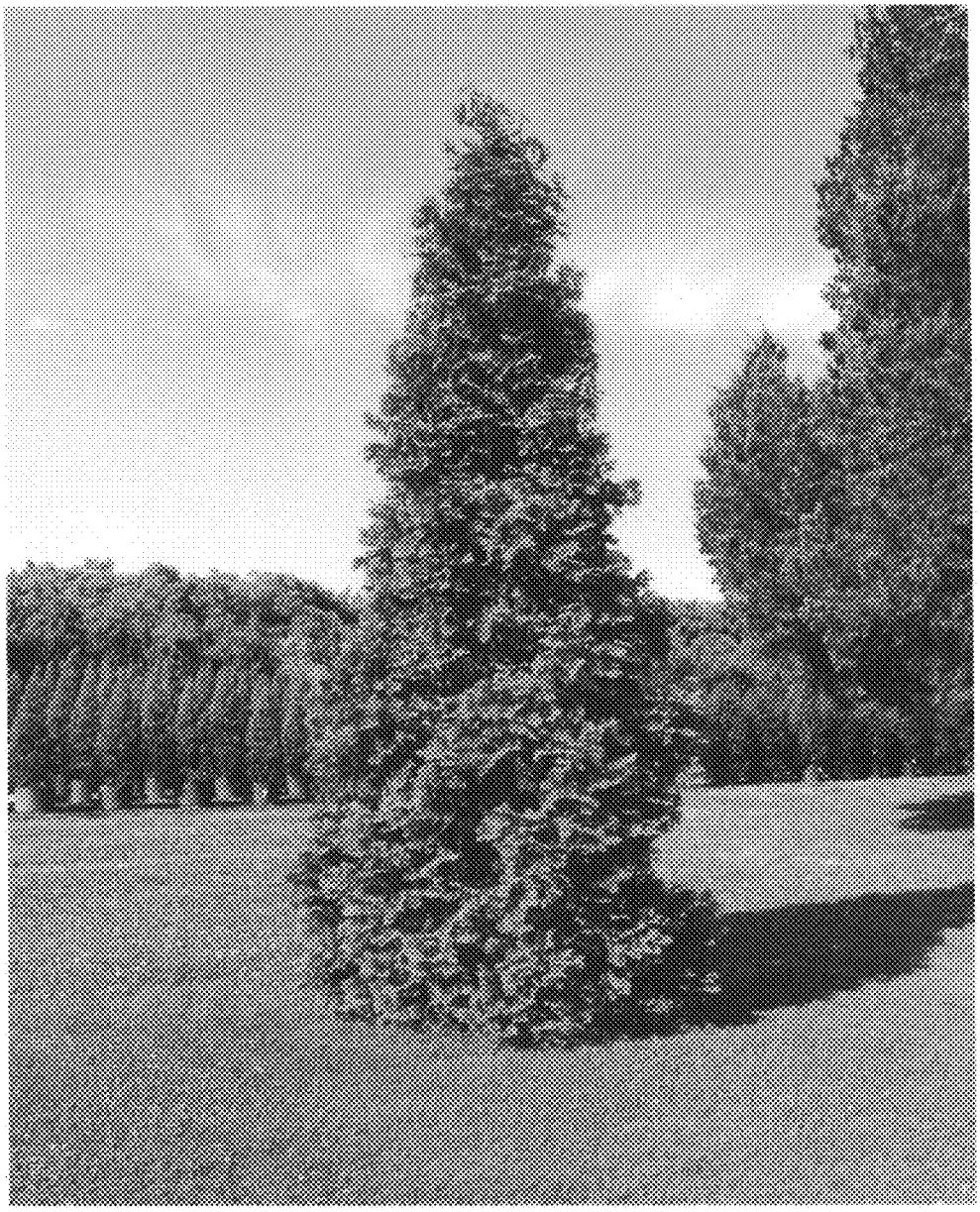
FIG. 1 shows an exemplary 'BFC68', in the ground and unpruned, at approximately 10 years old and standing approximately 4.25 m tall and 2 m wide.
Figure 2:
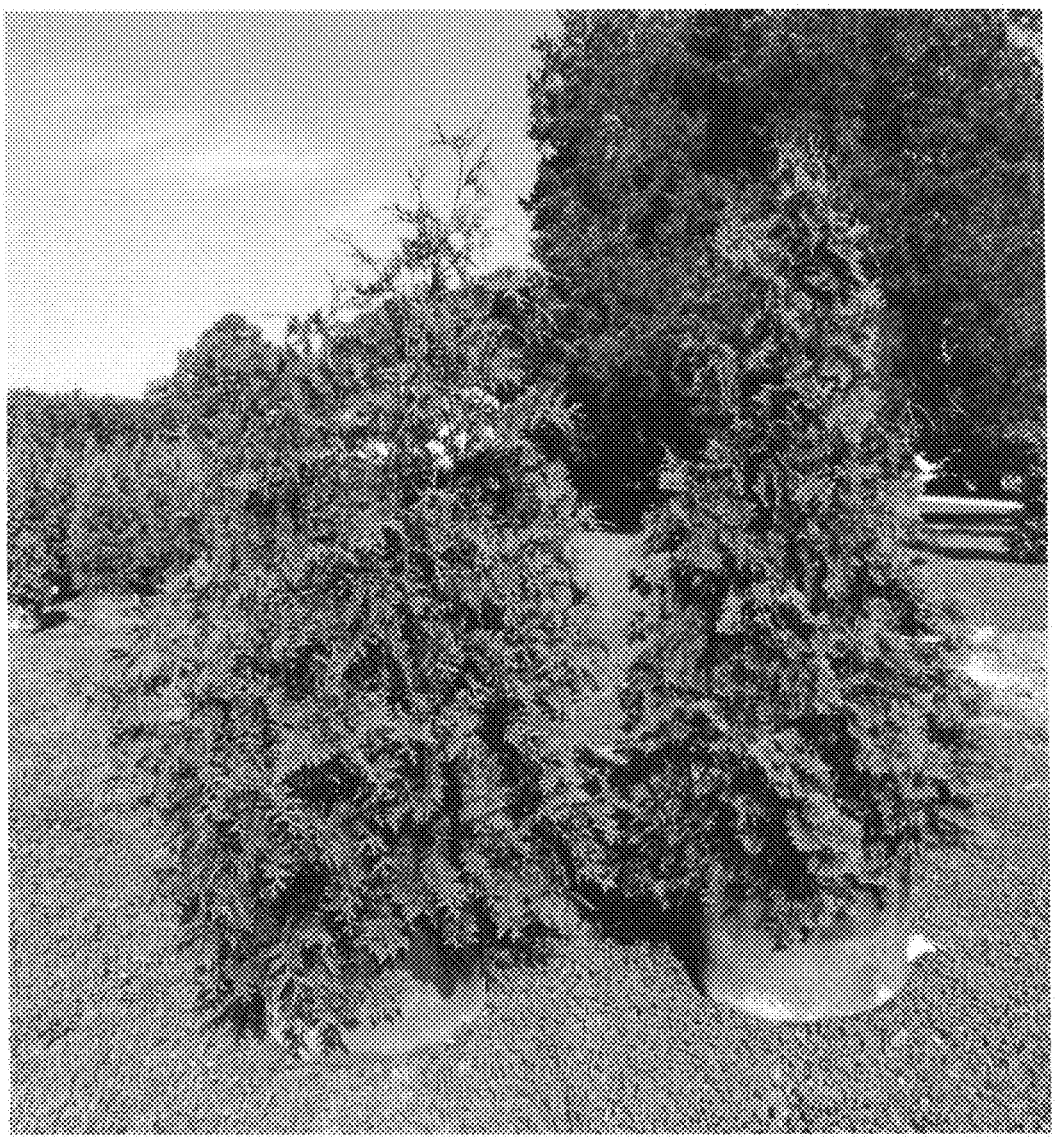
FIG. 2 shows a comparison of 'BFC68' (on right) and parent Green Giant (on left) of equal age, both having been potted in April of 2008 and now 5 years old. The 'BFC68' specimen has dimensions of 182 cm tall by 99 cm wide at the base whereas the 'Green Giant' specimen shown here measures 213 cm tall by 132 cm wide at the base.

The following is a detailed botanical description of a new and distinct variety of *Thuja plicata×standishii* known as 'BFC68' based upon observations of 33-month old plants grown from rooted cuttings into 15 gallon fabric nursery pots in full sun and in open beds in Suffolk, Va. during summer 2010 to spring 2013. Unless indicated otherwise, the descriptions disclosed herein are based upon observations made from said 'BFC68' plants grown in full sun from rooted cuttings filled with soilless potting media, maintained with granular slow release fertilizer, and regularly watered with overhead irrigation. No pest and disease measures were taken. Observation data was recorded in May of 2013 in Awendaw, S.C.

Those skilled in the art will appreciate that certain characteristics will vary with older or, conversely, with younger plants. 'BFC68' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 1986 edition.

A botanical description of 'BFC68' and comparisons with other varieties of *Thuja plicata×standishii* are provided below.

TECHNICAL DESCRIPTION OF THE VARIETY

Plant description:

- *Plant habit*.—Evergreen conifer with a conical shape and upright attitude.
- *Height*.—182 cm as measured from 4 year old specimens grown in 30 gallon nursery containers at Plantation Spring Nursery in Suffolk, Va. in May of 2013.
- *Width*.—99 cm as measured from 4 year old specimens grown in 30 gallon nursery containers at Plantation Spring Nursery in Suffolk, Va. in May of 2013.
- *Bloom period*.—Non-blooming.
- *Hardiness*.—USDA Zone 5 to 7.
- *Environmental tolerances*.—Similar to the parent plants; tolerates light shade, a wide range of soil conditions and drought tolerant once established.
- *Pest and disease susceptibility or resistance*.—In common with the species, none of note.
- *Propagation*.—Propagation is accomplished using softwood cuttings. Roots well without rooting compound or hormone.
- *Time to develop roots*.—Approximately 4 weeks at 70 degrees F.
- *Time to produce a rooted cutting*.—Approximately 24 weeks.
- *Crop time*.—Approximately 48 months are needed to produce a well rooted 30 gallon nursery container, from rooted cuttings.

Trunk, branches and branchlets:

- *Trunk color*.—A combination of greyed green 198D and 197D and also grey brown 199D; generally appearing closest to 197D and highly glaucous. Central leader, or terminal portion of the trunk, near apex closest to green 146A.
- *Trunk surface texture*.—Woody, with fibrous bark of irregular shape; color is generally grey brown 199D.
- *Branching habit*.—Freely branched along a central trunk with internode lengths ranging from 20 to 50 mm; these primary branches are lined with branchlets along their entire length, born in the lateral plane. Branch attitude is lateral to ascending; terminal portions of branches are slightly pendulous; all primary, secondary and tertiary branchlets are also slightly pendulous.
- *Branch shape*.—Cylindrical.
- *Branch surface texture*.—Woody and furrowed, with scaly bark; glabrous.
- *Branch color*.—Immature branches exhibit a combination of yellow-green 144A and 146B to greyed-yellow 162A. Mature branch color is a combination of greyed-orange 165A and greyed-green 197A; highly glaucous at all stages; scaly bark is greyed-orange 165A.

*Branch dimensions*.—Basal branches reach approximately 54 cm in length from trunk to last node; diameter is approximately 1.5 cm near the base.

*Internode length along lateral branches*.—Ranges from 10 to 20 mm with an average length of 13 mm.

*Branchlet description*.—Highly branched and consisting of primary, secondary, tertiary and also quaternary branchlets all of which tend to be overlapping; attitude is pendulous. Overall length of most mature branchlet is 45 mm. On average, these branchlets consist of 7.2 secondary branchlets (with a maximum number observed as 10 secondary branchlets), 21 tertiary branchlets (maximum of 22), and 10 quaternary branchlets (maximum of 11).

Foliage:

*Type*.—Evergreen.

*Shape*.—Oblanceolate.

*Division*.—Simple.

*Apex*.—Acute.

*Venation*.—Not discernable under 20-times magnification.

*Vein color* (*adaxial surfaces*).—Indistinguishable from surrounding foliage.

*Vein color* (*abaxial surfaces*).—Indistinguishable from surrounding foliage.

*Margins*.—Entire.

*Arrangement*.—Alternating facial and lateral leaves with lateral leaves folded around branches and branchlets.

*Attachment*.—Sessile; flattened and appressed along braches and branchlets.

*Texture*.—Smooth and glossy; abaxial surface is glandular.

*Surface hairiness* (*adaxial surface*).—Glabrous at all stages.

*Surface hairiness* (*abaxial surface*).—Glabrous at all stages.

*Mature leaf dimensions*.—Approximately 5 mm long and 2.5 mm wide (when unfolded).

*Leaf color* (*adaxial surface*).—Juvenile: yellow green 144A; mature: green 139A.

*Leaf color* (*abaxial surface*).—Juvenile: yellow green 144A; mature: green 139A.

*Petiole*.—None.

*Stipules*.—None.

Cone: Cone has not yet been observed.

Comparisons with other similar *Thuja* cultivars: When compared to the parent plant, other seedling accessions from the same parent cross as well as other cultivars known to the breeder; 'BFC68' displays an overall smaller plant size, a denser growth habit, a feathered foliage texture, and dense foliage at the plant's apex where normally there are few branches or branchlets. There are two commercially available cultivars, known to the breeder, that have a similar form as 'BFC68': *Thuja plicata×standishii* 'Green Giant' (unpatented) and *Thuja plicata×standishii* 'Steeplechase' (U.S. Pat. No. 16,094 P2).

While both 'BFC68' and 'Green Giant' are vigorous trees with a generally conical habit, there a number of significant differences that distinguish 'BFC86'. Those differences are described below.

'BFC86' is a smaller tree than 'Green Giant'. When comparing exemplary specimens of equal age (5 years old), 'BFC68' has dimensions of 182 cm tall by 99 cm wide, at the base, whereas 'Green Giant' measures 213 cm tall by 132 cm wide, at the base.

Figure 3:
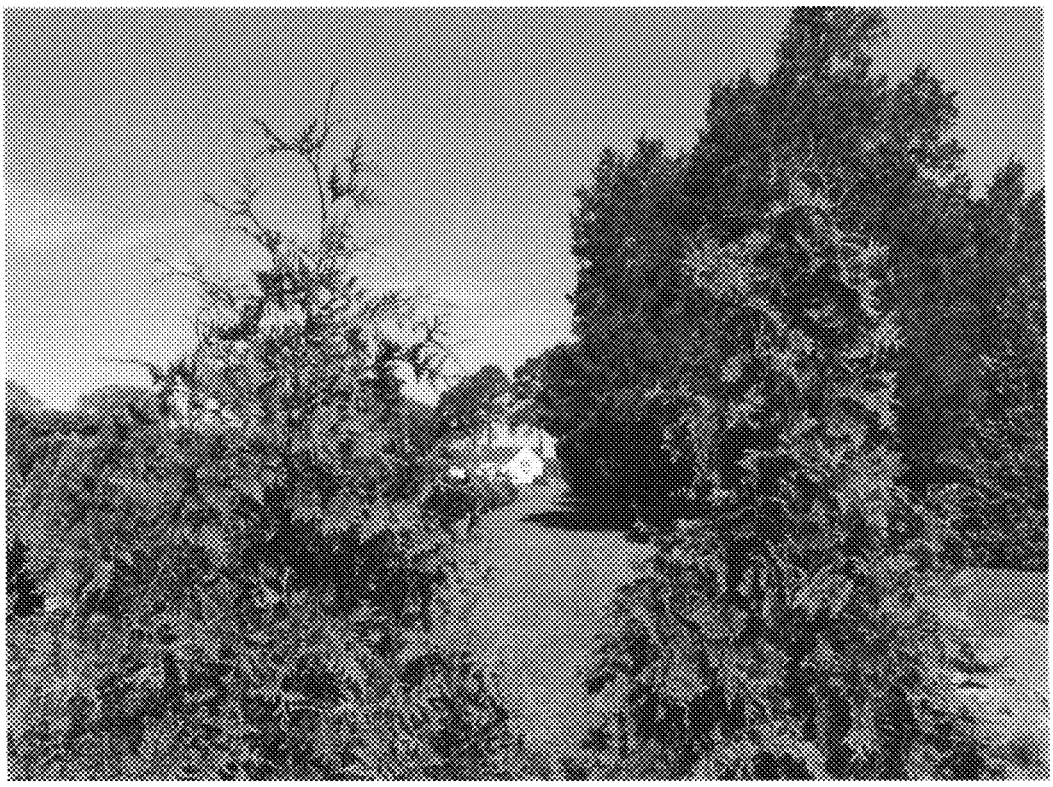
FIG. 3 shows the plant apices of those plants described in FIG. 2 with 'BFC68' on right and 'Green Giant' on left. Of note, is the dense apex and terminal portion of 'BFC68' compared to the parent which has few branches and branchlets.
Figure 4:
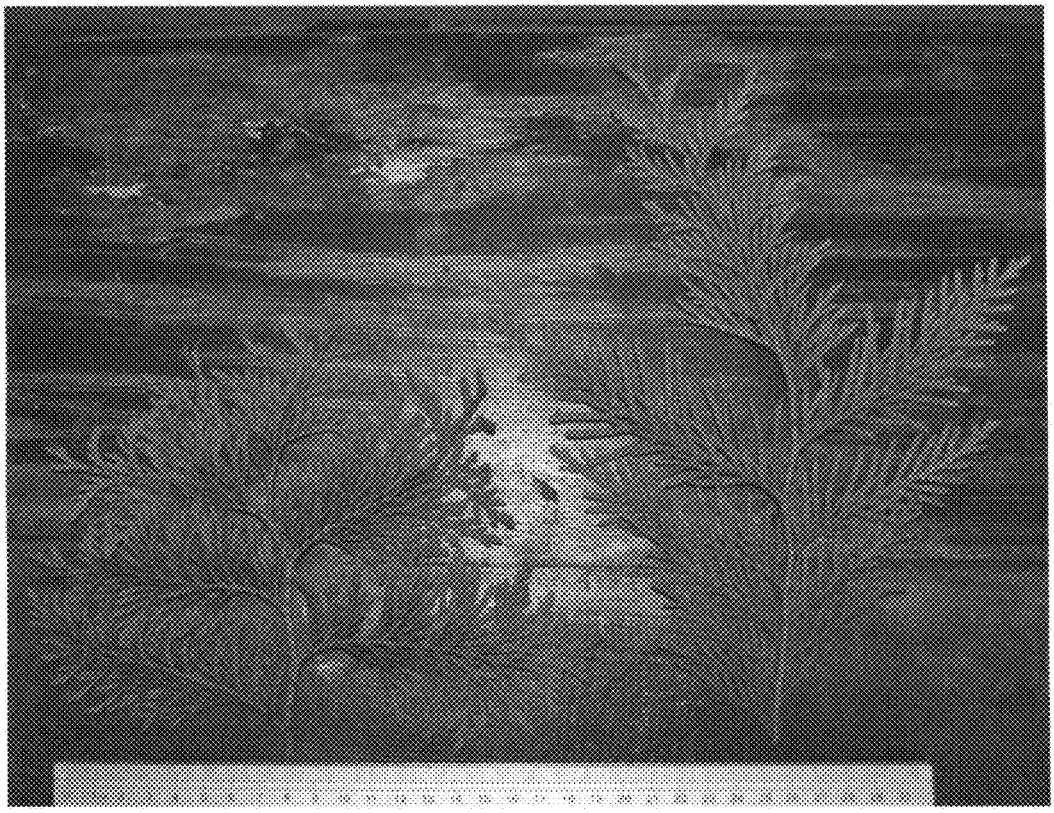
FIG. 4 shows a comparison of terminal portion of the lateral branches of 'BFC68' on left and 'Green Giant' on right. Of note is the high degree of branching on the primary, secondary and tertiary branchlets exhibited by 'BFC68'.

Referring now to FIG. 3, there is a significant difference in the apex density of 'BFC68' compared to 'Green Giant'. Young but marketable 'BFC68' plants (5 years old) have dense foliage at the plant's apex whereas 'Green Giant' plants of the same age have few branches or branchlets at or near the apex which gives 'BFC68'.

Figure 5:
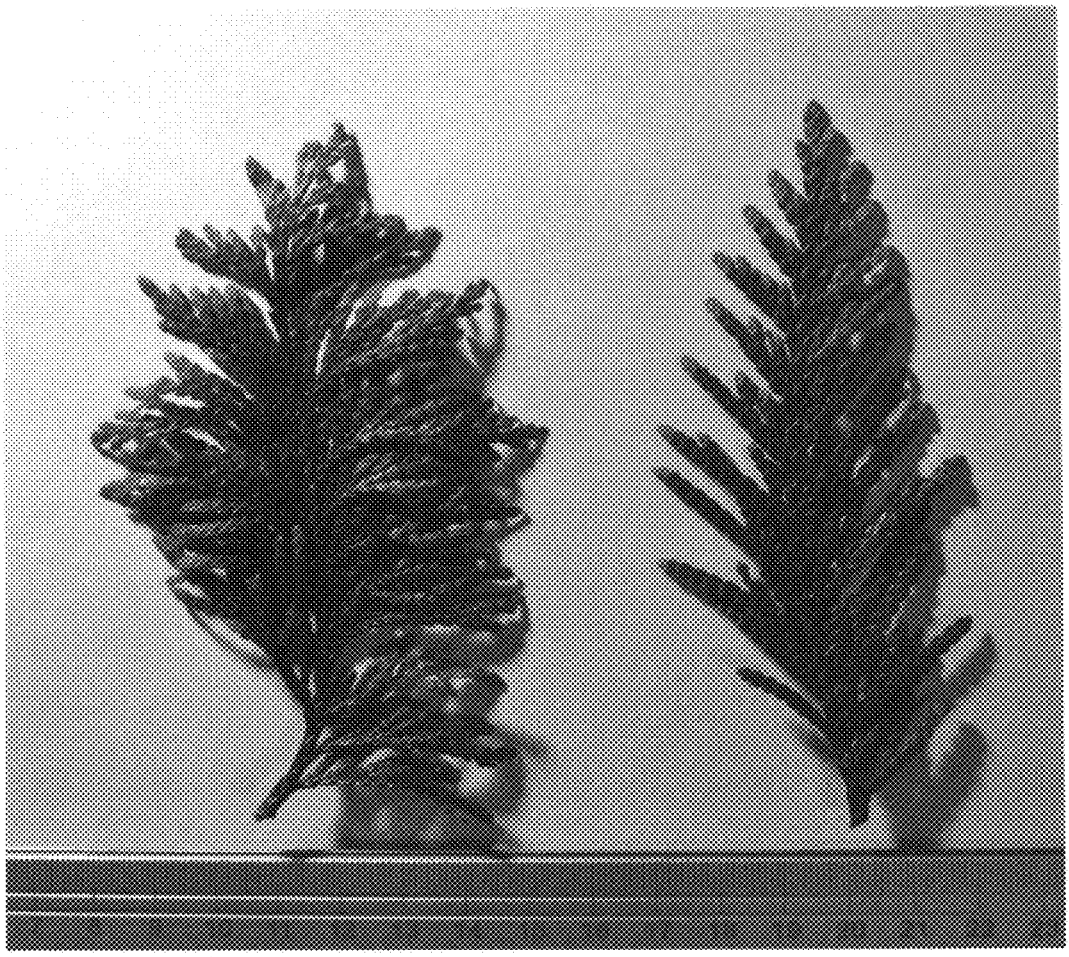
FIG. 5 shows a comparison of primary branchlets which arise from the lateral branches of both 'BFC68' (on left) and 'Green Giant' (on right). Of note is the high degree of branching of both the first and secondary branchlets exhibited by 'BFC68'.
Figure 6:
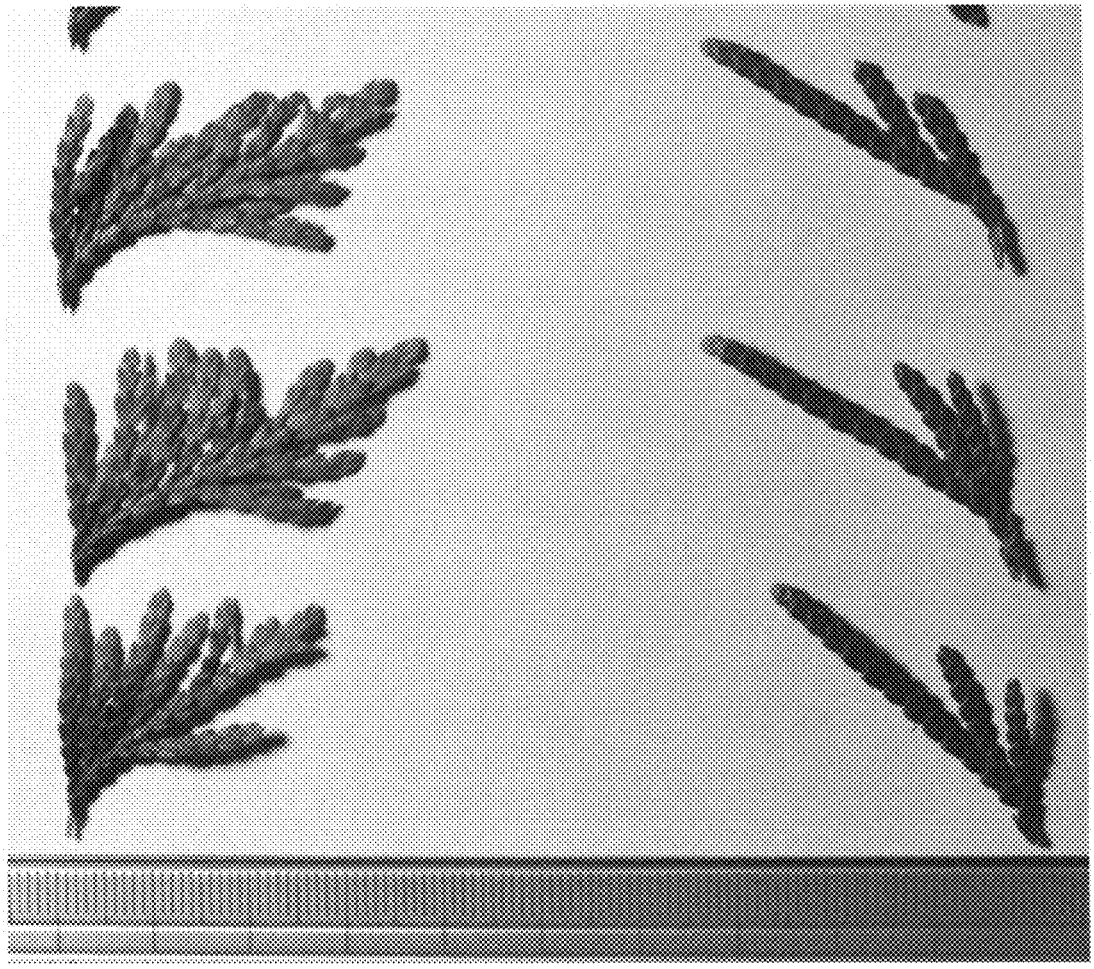
FIG. 6 shows a comparison of secondary branchlets of both 'BFC68' (on left) and 'Green Giant' (on right). Of note is the high degree of branching of the secondary branchlets exhibited by 'BFC68', with those secondary branchlets further branching to form tertiary branchlets which further branch to form quaternary branchlets.

The most significant difference between 'BFC68' and 'Green Giant' is in the branching habit of branchlets; said branchlets being borne along the lateral plane and at the terminal ends of those primary branches which arise freely from the central trunk. Referring now to FIG. 5 and FIG. 6; when compared to 'Green Giant', 'BFC68' exhibits a higher degree of branching among first, secondary and even tertiary branchlets whereas little branching is evident on branchlets of 'Green Giant'. With respect to branching of secondary branchlets, the average number of tertiary branchlets exhibited by 'BFC68' is 7.2 branchlets per secondary branchlet, compared to 'Green Giant' which only exhibits an average of 2.2 tertiary branchlets per secondary branchlet. 'BFC68' exhibits an average of 10 quaternary branchlets per secondary branchlet whereas Green Giant exhibits zero quaternary branchlets. Branchlet attachment of the tertiary branchlets to the secondary branchlets is also different between 'BFC68' and 'Green Giant'; attachment of said branchlets is alternate on 'BFC68' whereas tertiary branchlets of 'Green Giant' only occur on the ascending, outward plane of the secondary branchlets. This type of alternate attachment combined with the high degree of branching exhibited by 'BFC68' creates more overlapping of branchlets which adds to increased foliage density compared to 'Green Giant'.

While the length of primary branchlets is approximately the same for both 'BFC68' and 'Green Giant', the secondary and tertiary branchlets of 'BFC68' are longer. The length of the longest observed secondary branchlets on 'BFC68' average 45 mm in length whereas the longest primary branchlets of 'Green Giant' average only 38 mm in length. The tertiary branchlets of 'BFC68' have an average length of 21 mm whereas the average length of the tertiary branches of 'Green Giant' is 15.4 mm.

The branchlet attitude of the terminal portion of lateral branches and all branchlets of 'BFC68' is pendulous whereas the attitude exhibited by 'Green Giant' is ascending. This creates a soft, feathered foliage texture for BFC68.

While the scale-like leaves of 'BFC68' are similar to the parent, 'Green Giant', in both shape and color there are also some differences. The leaves of 'BFC68' are larger than those of 'Green Giant' with dimensions of approximately 5 mm long and 2.5 mm wide (unfolded), compared to 'Green Giant' with dimensions of approximately 3.5 mm long and 2 mm wide. While both varieties have dark green foliage there are differences here as well. The mature leaves of 'BNC68' are green 139A whereas the leaves of 'Green Giant' are yellow-green 147A. The immature leaves in both are closest to yellow green 144A. However, the higher degree of branching in 'BFC68' results in a greater quantity of immature foliage, meaning more of the yellow green immature foliage is present on 'BFC68'. By comparison with 'Green Giant', this creates a greater degree of contrast between the green mature foliage and the yellow green immature foliage.

As with 'Green Giant', 'BFC68' is similar to 'Steeplechase' in terms of vigor, form, habit and leaf characteristics but there are certain characteristics which distinguish 'BFC68' from 'Steeplechase'. Those differences are described below.

'BFC68' trees have a shorter height and are wider at the base than 'Steeplechase'; a 10 year-old 'BFC68' tree has dimensions of approximately 4.25 m tall and 2 m wide whereas 'Steeplechase' trees of similar age can be observed as 4.6 to 5.2 m tall and only 1.5 m wide.

While both 'Steeplechase' and 'BFC68' exhibit a pendulous branchlet attitude, this characteristic is more heavily pronounced in 'BFC68' which gives it a finer or more feathered texture than 'Steeplechase'.

The branchlets of 'BFC68' are more highly branched than those of 'Steeplechase'; 'BFC68' exhibits a high degree of branching among both the secondary and tertiary branchlets whereas 'Steeplechase' exhibits weak to no branching of the secondary branchlets and no branching of those tertiary branchlets that are present. Branchlet attachment of the tertiary branchlets to the secondary branchlets is also different between 'BFC68' and 'Steeplechase'; attachment of said branchlets is alternate on 'BFC68' whereas tertiary branchlets of 'Steeplechase' only occur on the ascending, outward plane of the secondary branchlets. This type of alternate attachment combined with the high degree of branching exhibited by 'BFC68' creates more overlapping of branchlets which adds to increased foliage density compared to 'Steeplechase'.

While the scale-like leaves of 'BFC68' are similar to the parent, 'Green Giant', in both shape and color there are also some differences. The leaves of 'BFC68' are smaller than those of 'Steeplechase' with dimensions of approximately 5 mm long and 2.5 mm wide (unfolded), compared to 'Steeplechase' with dimensions of approximately 5 to 7 mm long and 3 mm wide. While both varieties have dark green foliage there are differences here as well. The mature leaves of 'BNC68' are green 139A whereas the leaves of 'Steeplechase' are a lighter shade of green, 137A.

That which is claimed is:

1. A new and distinct variety of *Thuja plicata×standishii* plant named 'BFC68', substantially as described and illustrated herein.

* * * * *